United States Patent
Wilkening

(10) Patent No.: US 9,168,027 B2
(45) Date of Patent: Oct. 27, 2015

(54) ADAPTIVE ACOUSTIC PRESSURE ESTIMATION IN MEDICAL ULTRASOUND

(71) Applicant: Wilko Gerwin Wilkening, Mountain View, CA (US)

(72) Inventor: Wilko Gerwin Wilkening, Mountain View, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 127 days.

(21) Appl. No.: 13/774,885

(22) Filed: Feb. 22, 2013

(65) Prior Publication Data

US 2014/0243667 A1 Aug. 28, 2014

(51) Int. Cl.
*A61B 8/14* (2006.01)
*A61B 8/00* (2006.01)
*A61N 7/00* (2006.01)
*A61B 8/08* (2006.01)

(52) U.S. Cl.
CPC ... *A61B 8/58* (2013.01); *A61N 7/00* (2013.01); *A61B 8/481* (2013.01)

(58) Field of Classification Search
CPC ...... A61B 8/481; A61B 8/467; A61B 8/0841; A61B 8/12; A61B 8/08; A61B 8/52
USPC .................................. 600/437–469
See application file for complete search history.

(56) References Cited

U.S. PATENT DOCUMENTS

| | | | |
|---|---|---|---|
| 6,413,218 B1 | 7/2002 | Allison et al. | |
| 7,367,943 B2* | 5/2008 | Schluter | 600/438 |
| 7,993,273 B2* | 8/2011 | Phillips et al. | 600/458 |
| 8,021,303 B2* | 9/2011 | Frinking et al. | 600/458 |
| 8,043,219 B2 | 10/2011 | Chomas | |
| 8,391,949 B2* | 3/2013 | Schluter | 600/407 |
| 8,496,591 B2* | 7/2013 | Arditi et al. | 600/458 |
| 2005/0055178 A1* | 3/2005 | Phillips et al. | 702/189 |
| 2005/0154287 A1* | 7/2005 | Schluter | 600/407 |
| 2006/0030779 A1* | 2/2006 | Chomas et al. | 600/458 |
| 2008/0183066 A1* | 7/2008 | Schluter | 600/407 |
| 2008/0228080 A1* | 9/2008 | Arditi et al. | 600/458 |
| 2008/0294027 A1* | 11/2008 | Frinking et al. | 600/363 |
| 2010/0016719 A1 | 1/2010 | Freiburger et al. | |

OTHER PUBLICATIONS

F. Varray et al., "Acoustic nonlinearity parameter of tissue on echo mode: review and evaluation of the different approaches for B/A imaging," IEEE International Ultrasonics Symposium Proceedings, pp. 41-44, 2009.

H. Kim et al., "Estimation of Ultrasound Attenuation from Broadband Echo-Signals Using Bandpass Filtering," IEEE Transactions of Ultrasonics, Ferroelectrics, and Frequency Control, vol. 55, No. 5, pp. 1153-1159, 2008.

J. A. Jensen et al., "Simulation of non-linear ultrasound fields," IEEE Ultrasonics Symposium, pp. 1733-1736, 2002.

Y. Du et al., "Simulation of Second Harmonic Ultrasound Fields," IEEE International Ultrasonics Symposium Proceedings, pp. 2191-2194, 2010.

K. Samimi et al., "Ultrasonic Attenuation Imaging using Spectral Cross-Correlation and the Reference Phantom Method," IEEE International Ultrasonics Symposium Proceedings, pp. 53-55, 2011.

\* cited by examiner

*Primary Examiner* — Sanjay Cattungal

(57) ABSTRACT

Adaptive acoustic pressure estimation is provided in medical ultrasound. The responses of tissue of a specific patient at different frequencies (e.g., linear and non-linear responses) are measured. The responses are used to determine the acoustic pressure. The measurement in a specific patient adapts the estimate to the patient. The acoustic pressure for the desired locations is determined in order to set the transmit power to the desired level, such as for contrast agent imaging with high SNR but with limited destruction of the contrast agents or to provide the desired thermal dose the acoustic therapy.

19 Claims, 3 Drawing Sheets

ADAPTIVE ACOUSTIC PRESSURE ESTIMATION IN MEDICAL ULTRASOUND

BACKGROUND

The present embodiments relate to medical use of ultrasound. In particular, acoustic pressure of ultrasound adapts for diagnostic or therapeutic needs.

Ultrasound contrast agents are stabilized microbubbles. Contrast agents are pressure sensitive. High acoustic pressures destroy the microbubbles. In order not to destroy microbubbles, the transmit power is typically reduced by 10 dB-30 dB compared to typical B-mode imaging conditions. Moreover, the non-linear response of a microbubble may be weaker than the linear response of a scatterer in tissue. Thus, the signal-to-noise ratio (SNR) of contrast images is low, so using the maximum power that does not break the microbubbles is desirable.

Adjusting the transmit power to improve SNR or to minimize bubble destruction interferes with the data acquisition as the adjustment can only be performed after microbubbles have entered the imaging plane. Before a higher-quality acquisition may be repeated, the microbubbles have cleared the blood stream (e.g., about 15 minutes). Moreover, multiple injections of contrast agent are undesirable from a patient safety perspective and from a cost perspective.

In an attempt to set the transmit power before injection of contrast agents, clinicians use the mechanical index (MI) value as an indicator of acoustic pressure. While the MI is related to acoustic pressure, MI does not consider the patient's anatomy and does not provide information about the distribution of acoustic pressure in the imaging plane. Experienced clinicians may make adjustments based on the SNR of the B-mode image, but this is guesswork.

For ultrasound therapy, a desired thermal dose is to be applied to the patient. To much thermal dose may harm healthy tissue, and too little thermal dose may not fully treat the patient. However, various intervening structures may result in unexpected thermal dose. Like contrast agent imaging, the ability to predict the actual pressure is limited.

Other therapeutic applications may require certain acoustic pressure levels, for example to release drugs from microbubbles by destroying the shell or to establish stable cavitation.

BRIEF SUMMARY

By way of introduction, the preferred embodiments described below include methods, systems, computer readable media, and instructions for adaptive acoustic pressure estimation in medical ultrasound. The responses of tissue of a specific patient at different frequencies are measured. The responses are used to determine the acoustic pressure. The measurement in a specific patient adapts the estimate to the patient. The acoustic pressure for the desired locations is determined in order to set the transmit power to the desired level, such as for contrast agent imaging with high SNR but with limited destruction of the contrast agents or to provide the desired thermal dose or acoustic pressure for therapy.

In a first aspect, a method is provided for adaptive acoustic pressure estimation in medical ultrasound. First responses are acquired at a first frequency for a plurality of locations. Second responses are acquired at a second frequency for the plurality of locations. An acoustic pressure at one or more of the locations is estimated. The acoustic pressure is estimated as a function of the first and second responses. An acoustic output is set as a function of the acoustic pressure.

In a second aspect, a non-transitory computer readable storage medium has stored therein data representing instructions executable by a programmed processor for adaptive acoustic pressure estimation in medical ultrasound. The storage medium includes instructions for determining tissue response in first and second frequency bands to acoustic energy, setting a transmit power as a function of the tissue response in the first and second frequency bands, and performing contrast agent imaging or acoustic therapy using the transmit power.

In a third aspect, an ultrasound system is provided for adaptive acoustic pressure estimation in medical ultrasound. A transmit amplifier connects with a transducer. A processor is configured to establish a transmit power of the transmit amplifier as a function of a first amplitude profile as a function of depth at a first frequency and a second amplitude profile as a function of depth at a second frequency different from the first frequency.

Further aspects and advantages of the invention are discussed below in conjunction with the preferred embodiments. The present invention is defined by the following claims, and nothing in this section should be taken as a limitation on those claims.

BRIEF DESCRIPTION OF SEVERAL VIEWS OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF THE PREFERRED EMBODIMENTS

Ultrasound contrast imaging requires careful adjustment of the acoustic output power to avoid destruction of the agent and to maximize sensitivity. Acoustic pressure lower than optimal may result in reduced sensitivity and/or penetration. Acoustic pressure higher than optimal may result in too much destruction of the contrast agents. Similarly, ultrasound therapy benefits from precise setting of the acoustic energy to provide the desired dose or pressure.

Ultrasound propagation in biological tissue is non-linear, resulting in multiple spectral components in the received echo signal. By analyzing the amplitudes of spectral components that have different dependencies on the transmitted acoustic pressure, such as linear and quadratic, the acoustic pressure in a target organ may be estimated and adjusted to optimize contrast imaging or acoustic therapy.

For example, the acoustic pressure inside the body may be estimated by measuring intensity profiles (intensity vs. depth) for the fundamental and the harmonic (e.g., second) component of received echoes. The fundamental and the harmonic responses are determined at multiple locations in the imaging plane or volume. This determination may occur in less than one or a few minutes before arrival of contrast agents at a region of interest, so adds little time to an ultrasound examination. The absolute acoustic pressure is estimated for at least one location from the responses. The acoustic output is adjusted or otherwise set in response to the pressure estimate to achieve optimal contrast image quality.

Tissue may be 'dark' because there is not much sound getting there or because the tissue does not scatter much. The non-linear propagation is not much affected by scattering. This is why a strong second harmonic compared to the fundamental may result from 'dark' tissue, indicating that the acoustic pressure is actually high. By accurately predicting the pressure, more about the echogenicity of the tissue is determined.

Figure 1:
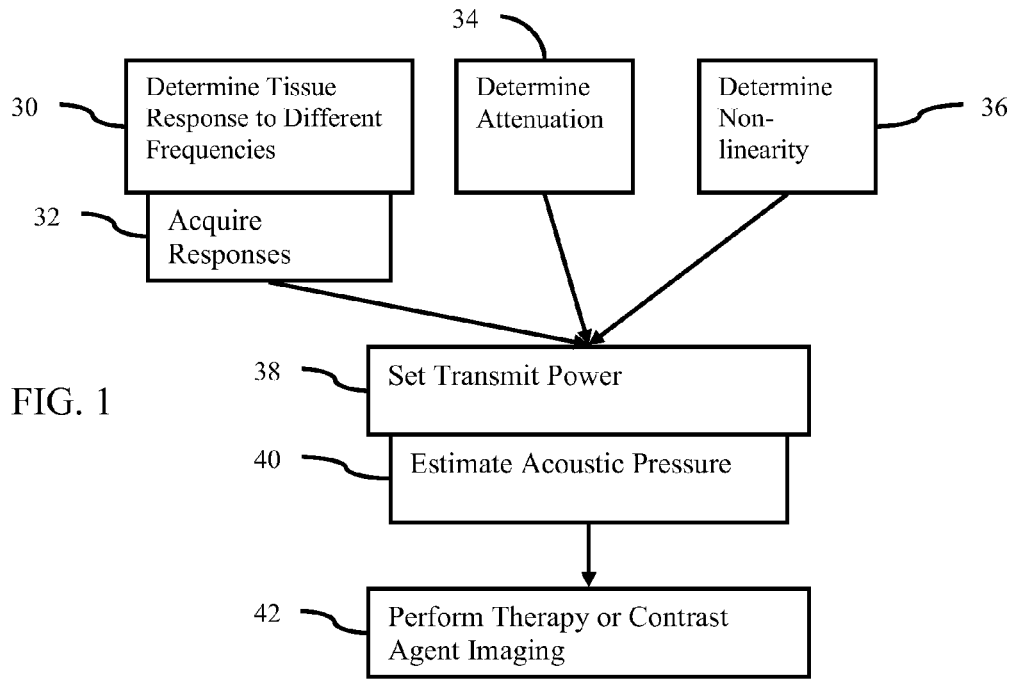
FIG. 1 is a flow chart diagram of one embodiment of a method for adaptive acoustic pressure estimation in medical ultrasound.

FIG. 1 illustrates one embodiment of a method for adaptive acoustic pressure estimation in medical ultrasound. The responses to ultrasound of tissue at different frequencies are used to estimate acoustic pressure. The transmit power for subsequent transmissions is set based on this acoustic pressure. The adaptation for acoustic pressure may set the transmit power based on the responses at different frequencies without a direct estimation of the acoustic pressure.

The transmit power is set for any ultrasound transmission. For example, the transmit power is set for therapy to more likely provide the desired dose. As another example, the transmit power is set for contrast agent imaging to improve SNR while minimizing or avoiding destruction of the contrast agents in a desired region.

Figure 4:
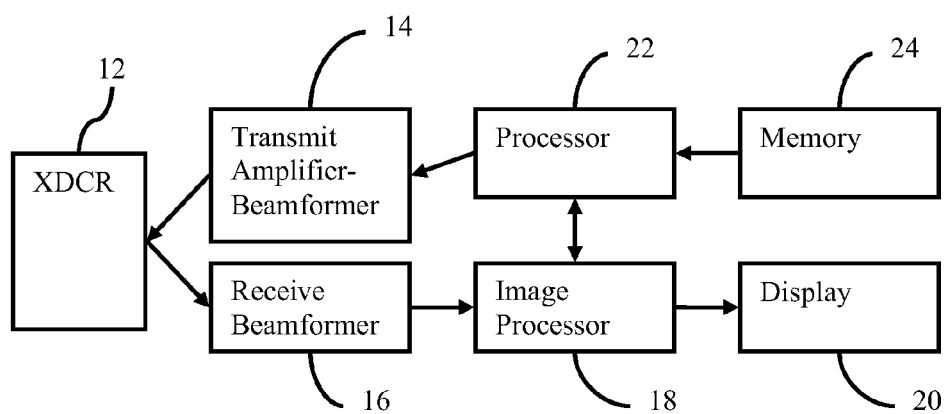
FIG. 4 is a block diagram of one embodiment of a system for adaptive acoustic pressure estimation in medical ultrasound.

The method of FIG. 1 is implemented with the system of FIG. 4, but other systems may be used. A medical diagnostic imaging system performs the method. Alternatively, an ultrasound therapy system performs the method. In yet other embodiments, a computer connected with a transducer with or without extra beamformer electronics performs the method.

The method is performed in the order shown or a different order. For example, acts 30, 34, and 36 are performed in any order or simultaneously. Additional, different, or fewer acts may be provided. For example, one or both of acts 34 and 36 are not performed. As another example, act 42 is not performed. Act 40 may not be directly performed, such as where the information indicative of acoustic pressure is used to set the transmit power level without a specific estimation of the actual acoustic pressure. In yet another example, a configuration act and/or one or more acts for gathering further measures or values to estimate acoustic pressure are performed.

The transmit power setting feature is initiated automatically or manually. For example, a user depresses a button, depresses a foot pedal, selects a menu item, or speaks (e.g. control through voice activation). As another example, the user selects contrast agent imaging software or software specific to a contrast agent imaging application. As yet another example, the request is generated by continuously active software. Contrast agents are injected into a patient before or after the request. In response to the request, any current imaging is interrupted or interleaved with the acquisition of data for setting the transmit power level.

In act 30, the response of tissue to acoustic energy is determined. Responses are determined for different frequencies. The different frequencies are different center frequencies and/or different frequency bands. The frequency bands may or may not overlap. The ratio between, for example, the second harmonic echo amplitude and the fundamental echo amplitude provides an indication of the absolute fundamental sound pressure inside the tissue.

Act 30 is performed by acquiring the responses at the different frequencies in act 32. In act 32, ultrasound echo data are acquired. For example, transmissions and receptions to satisfy the detection technique (e.g. multiple pulses for each fundamental datum, multiple pulses for each harmonic datum, or a single pulse for B-mode) are performed for one or more locations. In one embodiment, four or more pulses are used to derive the fundamental excluding the second harmonic and the second harmonic excluding the first harmonic from the four or more echoes.

The locations may be along a scan or beam line and/or distributed among different scan lines in plane or volume. For the same scan line, a same transmit and corresponding receive operation may be used to obtain the response at different locations. For locations along separate scan lines, sequential transmit and receive operations to the different scan lines are used. Alternatively, a wide beam or multiple beam transmit and corresponding multi-beam receive operations are performed.

The locations may be at the sampling density for imaging or a sub-set of such locations. Fewer locations may demand less processing and/or scanning time, so in one embodiment the line density is a factor of one to four less dense than is used for B-mode tissue imaging. Other line or sample densities can be used, such as performing the measure along one scan line for the plane or volume. For each given line, any sampling density may be used. For example, the same sampling density as used for B-mode imaging is used. Echo signals from various depths along the scan line are acquired.

The scan line or lines used for sampling and the sample locations along the lines are selected as regions with known backscatter characteristics, such as fully developed speckle. In the liver, most of the organ is soft tissue, so has known backscatter characteristics. The locations are selected as soft tissue locations rather than large vessel or vein locations. In alternative embodiments, the locations are associated with other types of tissue or structure.

The path of propagation may be considered as well. Beams or scan lines that only propagate through tissue that shows fully developed speckle are used. Beams intersecting or passing through a vessel, bone, hard tissue, or fluid tissue to arrive at the sample locations are not used. Alternatively, beams passing through other types of tissue are used. In many cases, the tissue in the near-field does not matter as long as the near field does not include a bone and as long as is generally or in average the same as the tissue being measured. The samples are taken along a range of the beam that is 'homogeneous'.

The locations and/or scan lines are selected manually or automatically. For example, a user indicates the sample locations and/or beams to use on a B-mode or B-mode and flow mode combination image. As another example, the signal-to-noise ratio (SNR) is determined for locations throughout a plane and/or volume. Speckle is associated with (spatial) variance in the SNR. Where the ratio of the mean variance to the standard deviation is about 1.9, a speckle region associated with soft tissue is indicated.

The responses for the locations are acquired at two or more different frequencies. In one example used herein, the fundamental or transmit frequency (e.g., 2 MHz) and a second harmonic (e.g., 4 MHz) of the fundamental frequency are used. The fundamental response serves as a measure of echogenicity.

Instead of the fundamental (first harmonic) and second harmonic response, other combinations of two or more harmonics may be used to estimate absolute acoustic pressures.

Any combination of signal components related to different terms in the non-linear wave equation may be used, such as the second harmonic and the cubic fundamental.

To isolate the response at the different frequencies, the received signals representing acoustic echoes are processed. The same data is used to determine the responses at the different frequencies. For example, the echo signal is decomposed by filters in order to determine the amplitudes of the reflected harmonic waves. The unfiltered signals are used for the fundamental, but filtering may be used. As another example, coded transmit pulse sequences (e.g., pulse inversion) are employed. For pulse inversion, the amplitudes of two otherwise identical transmit pulses are [1, −1]. By subtracting the receive signals, contributions from even order harmonics are canceled, providing information at the fundamental frequency. The information at the other odd harmonics are relatively small so may remain, but may be filtered out in other embodiments. By adding the receive signals, contributions from odd order harmonics are cancelled. Similarly, the information at other even harmonics than the second harmonic are small, so may remain, but may be filtered out. Any additional filtering may improve the separation between the harmonic components and reject noise. Sequences with three or more transmit pulses with different phases, amplitudes, or phases and amplitudes followed by combination (e.g., weighting and filtering) on reception may be used to isolate information at desired bands.

In alternative embodiments, different transmission and reception events are used to acquire the different responses. For example, a transmit pulse and corresponding receive operations are performed for obtaining response at the locations for the fundamental frequency. A separate or sequential transmit and receive operation is performed for obtaining the response at the locations for the different fundamental or harmonic frequency.

The response is amplitude as a function of location. For example, the response is amplitude as a function of depth. Beamformed samples before or after detection are used. For example, beamformed samples after intensity or B-mode detection are used. Any depth gain correction or compensation applied by the beamformer may be removed. Alternatively, the depth gain correction is not provided in the first place. In yet other embodiments, the depth gain correction is consistently applied and the resulting signals are used without removal of the gain.

Figure 2:
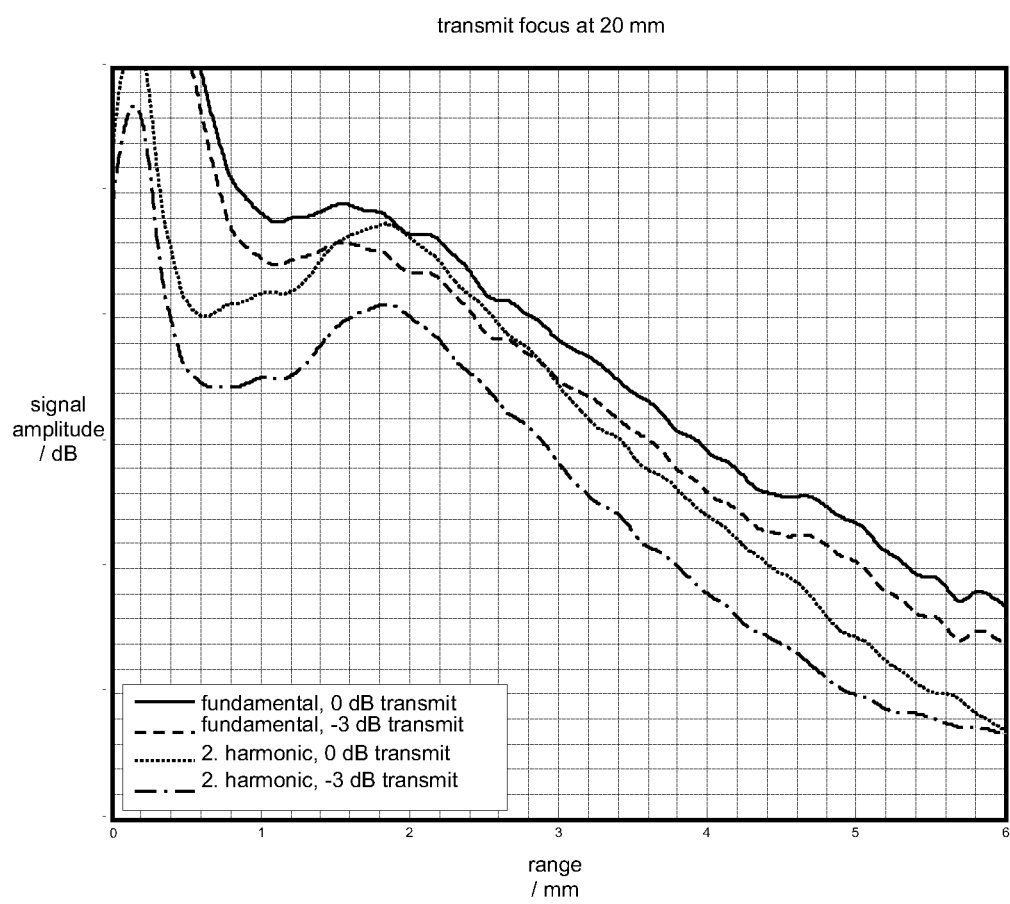
FIG. 2 is a graphical representation of example amplitude profiles at different receive frequencies and transmit power levels.

The amplitude as a function of depth is acquired with a same transmit focal location. Dynamic receive focusing is used, but a single receive focus may be provided. FIG. 2 shows example responses with a transmit focus at 20 mm. Other transmit focal depths may be used, such as the 40 mm focus shown in FIG. 3.

Figure 3:
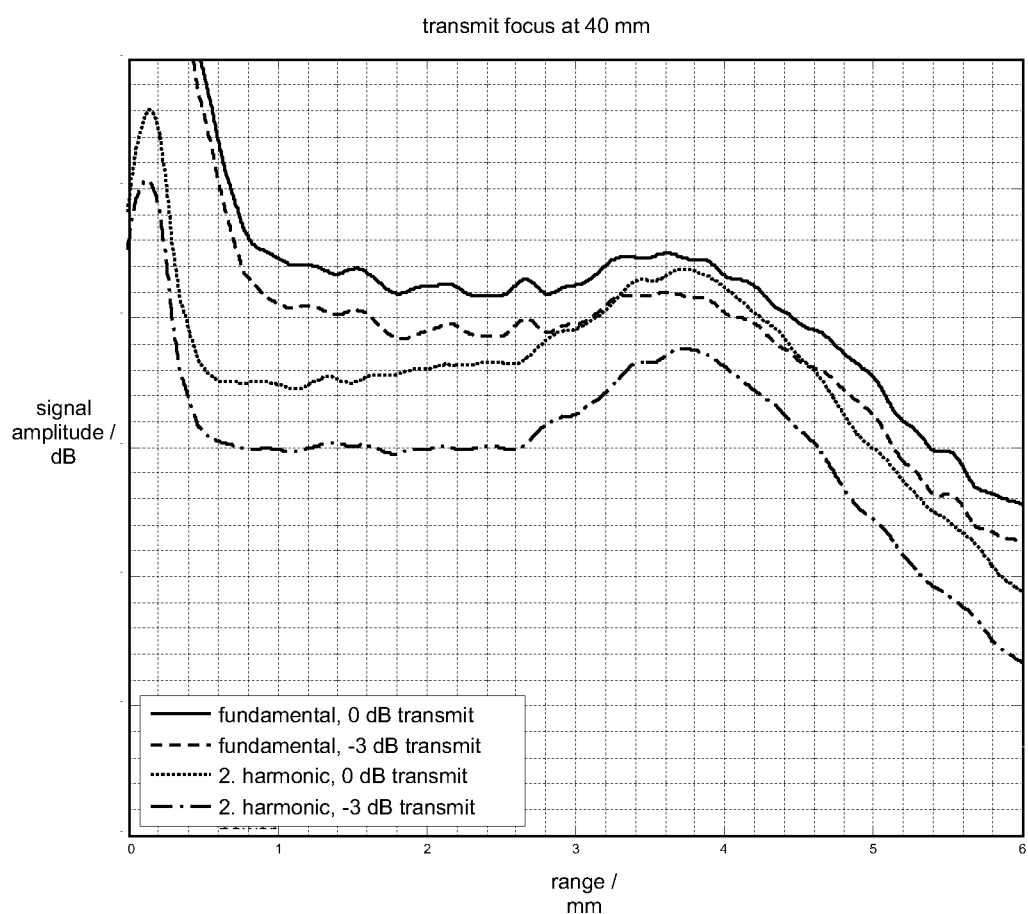
FIG. 3 is a graphical representation of other example amplitude profiles at different receive frequencies and transmit power levels, but with a different transmit focal depth than for FIG. 2.

The amplitude as a function of depth is provided for the two or more frequency bands. FIGS. 2 and 3 show responses for the fundamental and second harmonic frequencies.

To improve accuracy of estimation or setting, the responses at different transmit foci may be acquired in sequential transmit and reception events. For example, the responses of both FIGS. 2 and 3 are acquired. The transmit focus depth is varied to gather measurements at different depths to confirm assumptions regarding B/A (non-linear parameter where B and A are the first two coefficients of a Taylor series describing the dependency of the speed of sound on the local pressure), attenuation, and the absolute sound pressure at different depths.

The responses are to transmissions at a given transmit power. In alternative embodiments, responses at the different frequencies are acquired for each of different transmit powers. The amplitude as a function of location (e.g., depth) is determined for each of different transmit levels. FIGS. 2 and 3 show an example of two responses for each frequency where the two responses correspond to two transmit powers. One transmit power is −3 dB down from the other, but a smaller or greater difference may be used. More than two different transmit power levels may be used. The responses for the different transmit power levels are acquired sequentially, such as in response to different transmit events.

FIGS. 2 and 3 illustrate some of the phenomena for estimating acoustic pressure. When reducing the transmit power by 3 dB, the signal level of the second harmonic drops by 6 dB for well separated responses at the fundamental compared to the second harmonic. Without pulse inversion and narrow pulses, the second harmonic may only drop by 4 dB when the transmit signal level is reduced by 3 dB because of fundamental leakage. At a certain depth, the squared behavior may no longer apply because the second harmonic drops close to the noise floor. By analyzing the two curves at two power levels, the system may identify the SNR limit.

The second harmonic level increases rapidly close to the focal depth. The ratio (difference in dB) between the second harmonic and the fundamental increases with increasing transmit power. The slopes for the second harmonic signal and the fundamental signal beyond the focal depth differ as result of differences in beam pattern and attenuation. The examples of FIGS. 2 and 3 are of echo intensity of a tissue mimicking material as a function of depth, but the response from an actual patient are used in other embodiments.

In act 34, the attenuation is determined. Attenuation may be used to more accurately determine the ratio of the responses at different frequencies. The attenuation may be used for estimating the acoustic pressure.

The attenuation may be an assumed or predetermined value. For example, attenuation may be a value based on the type of tissue. The user indicates the type of tissue, such as selecting a liver imaging application. The type of tissue may be determined from ultrasound signals and used to select the predetermined attenuation value. Attenuations for the beam path through various types of tissue may be used. Alternatively, the attenuation is a predetermined value associated with soft tissue in general rather than a specific type of tissue.

In other embodiments, the attenuation is determined from the acquired responses or other ultrasound measures. For example, the attenuation is determined from the slope of the responses at the different frequencies. The slopes of the fundamental and harmonic signals before and after a maximum are determined. The maximum of the amplitude is at or near the transmit focus. Any near field maximum may be ignored.

In tissue, attenuation is approximately proportional to frequency. The harmonic waves suffer from higher attenuation. Ultrasonic imaging typically uses focused beams. If the f-number is low, the pressure of the fundamental wave increases towards the focus and reaches a maximum close to or at the focus. As the amplitude of the fundamental wave increases, the amplitudes of harmonic waves increase rapidly because of the non-linear and accumulative nature of the phenomenon. After having reached a maximum, the amplitudes of the harmonic waves decrease rapidly because conversion from the fundamental wave diminishes and because the harmonic waves are subject to higher attenuation. At a given location along an ultrasound beam, the amplitude of the fundamental wave is proportional to the transmitted wave, ignoring fundamental depletion, and the amplitude of the second harmonic wave is approximately proportional to the amplitude of the transmitted signal squared.

The ratio of the slopes of the responses, given a Gaussian transmit pulse, indicates the attenuation. The slope is from the far field region, such as fitting lines to the responses after the maximum. A relatively shallow transmit focus may be used, such as the 20 mm focus. The near field or ratio at the maximum or other discrete depth may be used in other embodiments. Attenuation at different depths may be calculated. Other calculations of attenuation may be used, such as observing the downshift of the center frequency verses depth. Measuring at two or more different transmit frequencies may be used.

In act 36, a value for a non-linearity parameter is determined. Wave propagation in biological tissue or fluids is non-linear. Non-linear propagation causes a waveform to be distorted as the waveform propagates through the medium. The distortion increases with the distance that the wave travels. As the distortion is a non-linear effect, distortion also increases with amplitude.

The distortion may also be described as the generation of harmonics waves with frequencies that are integer multiples of the frequency of the undistorted wave (i.e., the fundamental frequency). The energy of the harmonic waves is from the fundamental wave due to conservation of energy. However, the conditions in diagnostic ultrasound are such that the harmonic waves are much weaker than the fundamental wave and such that the loss in amplitude of the fundamental wave (i.e., fundamental depletion) may not be measurable.

The fundamental and harmonic waves are reflected by interfaces between media or scattered by scatterers and propagate back towards the transducer forming echo signals. These echoes are generally weak enough so that non-linear propagation is negligible. Scattering is frequency dependent. However, scattering does not depend on amplitude (i.e., scattering is linear), and the frequency dependency for a certain type of tissue may be determined by an ultrasound measurement (e.g. pulse-echo measurements with two transmit signals having different frequencies).

The non-linearity may be expressed as the speed of sound as a function of the local pressure. The non-linearity is often characterized by the ratio B/A, where B and A are the first two coefficients of a Taylor series describing the dependency of the speed of sound on the local pressure. B/A depends on the tissue type, and the amplitudes of the harmonic wave depend on B/A. B/A is measured using pulse-echo techniques. The responses or other ultrasound data is used. Alternatively, values for certain organs are found in the literature. A predetermined non-linearity parameter value is selected by the user or used based on detected type of tissue. The value may be based on the type of tissue being scanned.

In act 38, a transmit power is set as a function of the tissue response in the different frequency bands. The transmit power may be set based on responses at different powers and/or transmit foci as well. The attenuation and/or non-linearity parameter values may also be used for setting the transmit power. Additional, different, or fewer inputs may be used.

The transmit power is set based on acoustic pressure. The transmit power may be set using inputs indicative of acoustic power, such as the responses at different frequencies. Alternatively and as reflected by act 40, the acoustic pressure may be estimated, and the estimate of pressure used to set the transmit power. The acoustic pressure is estimated as a function of the tissue responses at different frequencies, an attenuation, and an ultrasound non-linearity parameter.

To take another example, characteristics of the response may be used instead of or in addition to the responses. A slope, mean, difference, or other characteristic of the amplitude as a function of locations may be calculated. The characteristic may be calculated for each response or may be relative (e.g., represent a similarity or difference between the responses). As another example, transmit beamformation parameters are used. The focal depth, apodization characteristic, aperture size, acceptance angle of the elements on transmit and receive, angle of the transmit and/or receive beam to the array, and/or other parameters representing beamformation may be associated with an amount of pressure.

The acoustic pressure is estimated for at least one of the locations for which the response is sampled. For example, the acoustic pressure is estimated for the transmit focus, but shallower or deeper locations may be used. The acoustic pressures may be estimated for multiple locations.

The inputs are provided to a model. The model outputs the acoustic pressure in response to the inputs. The model is a forward model, but machine-learnt models may be used. For example, a real-time simulation is used to search for acoustic pressure, B/A, and attenuation values by matching the simulation results to the measured responses.

In another embodiment, the model is represented by a look-up table or database. The acoustic pressure is looked-up based on the responses at different frequencies, parameter values derived from the responses, attenuation value, and/or non-linearity parameter value. Two or more inputs associated with different frequencies (e.g., responses at different frequencies) are used for looking up the output estimate. By comparing the amplitude profiles or parameters derived from such profiles to a lookup table or database, the absolute acoustic pressures may be determined as a function of depth or other location distribution.

The values in the database or look-up table are experimentally determined and/or simulated. For example, the lookup table is generated through simulation using the KZK equation or an array simulator (e.g., Field II) with a non-linear propagation add-on.

The simulation or experimentally determined look-up table may include inputs for the non-linearity parameter and/or attenuation. Alternatively, separate tables are provided for different non-linearity parameter and/or attenuation values. Any combination of combinations of tables or a combined table may be used.

In yet another embodiment, the model represents the expected responses at different frequencies for a given transmit configuration and tissue. The responses are acquired at different transmit powers. The transmit power is varied until the responses best or sufficiently match the expected responses. The transmit power associated with the match provides the expected relationship between acoustic pressure and transmit level.

The model outputs the acoustic pressure and/or the transmit power. The acoustic pressure at a location is estimated based on responses at different locations and/or the same location.

Due to attenuation, the acoustic pressure at different locations is different. The acoustic pressure at different locations may be estimated by the model. For example, the inputs for the location are provided to the model. Alternatively, the acoustic pressure at other locations is determined based on another estimated acoustic pressure. Given an attenuation value, acoustic pressure at one location may be use to determine pressure for other locations. The attenuation provides a scaling factor for estimating pressure caused by a same transmit event.

In act 38, the transmit power is set based on the acoustic pressure. Once the acoustic pressure is determined, the transmit power for contrast agent medical diagnostic imaging, therapy, or other use is set. A look-up table, function, or other model relates the acoustic pressure to the transmit power level. The setting may be an absolute value or an amount of change. The setting may occur once or may be an iterative process where different transmit levels are used until a desired pressure results.

In one example, the acoustic output for transmit operation is set to avoid destruction of contrast agents while attempting to have a substantially maximum output. Substantially accounts for deviation or a tolerance to provide a margin for error, such as 10%. Due to variation in contrast agents and/or inaccuracy in pressure estimation, a tolerance is provided to avoid destruction of a majority of the contrast agents in a region of interest. By estimating the acoustic pressure at the region of interest, the transmit power resulting in a non-destructive but good SNR pressure may be provided. The estimate adapts to the patient, system, and/or beam path variation.

In another example, the acoustic output for transmit operation is set to provide a desired dose. The thermal dose corresponds to the acoustic pressure applied at the region of interest. By estimating the acoustic pressure at the region of interest, the transmit power results in a desired thermal dose less likely to harm healthy tissue but still able to fully treat unhealthy tissue. The estimate adapts to the patient, system, and/or beam path variation.

In one embodiment, the transmit power is set based on inputs in addition to the estimated pressure. For direct setting of the transmit power without separately estimating the pressure, the additional inputs may be included in the model to output transmit level. Otherwise, a further calculation or look-up function is performed. The setting accounts for the transmit level used to generate the pressure and a relationship of transmit level to pressure. Any additional inputs may be used.

One input is noise. The noise may be measured. For example, the receive signals are measured without any transmit event. Any noise measurement may be used.

Another input is the type of contrast agent, the desired dose over a given time, or other use of the transmit for which the level is set. For example, different contrast agents may be destroyed at different threshold amounts of acoustic energy or pressure. The level associated with destruction is relative as variation in microbubbles may result in some destruction at most any level. The pressure and corresponding transmit level at which 10%, ⅓, or other measure of contrast agent is destroyed may be different for different types of contrast agents. By indicating the type of contrast agent, a corresponding desired pressure level is indicated. As another example, the thermal dose to be applied may depend on the type of therapy, the size of the region to be treated, and the proximity of any heat sinks (e.g., blood vessels). The resulting pressure and corresponding transmit level may be different for different therapy situations.

Based on the analysis of the acoustic pressure distribution in the imaging plane, the type or characteristic of contrast agent, and the noise floor measurements, the transmit power setting is selected. Additional optimization criteria may be set by the clinician and/or predetermined based on the application. For example, the power level may be set based on the pressure to satisfy a specific criteria, such as best SNR, minimal destruction, or maximum penetration.

In addition, the algorithm may optimize other parameters of the transmit pulse, such as center frequency and/or bandwidth. Receive processing parameters, such as receive bandwidth and/or gain, may be optimized since the receive spectra and SNR may be predicted or modeled based on the measured parameters. Knowing the acoustic pressure and attenuation, the transmit focusing may also be adapted.

In act 42, imaging or therapy is performed. The imaging or therapy includes transmitting acoustic energy. The acoustic energy is transmitted at a power level set in act 38. For example, one or more transmissions are performed for imaging contrast agents in a liver. Enhancement patterns in the arterial phase and the portal-venous phase are used to diagnose lesions. The patterns are detected or viewed based on responses to the transmissions at the set power level. One or more images of contrast agent are displayed to the user. In one embodiment, the mechanical index or power level is indicated to the user on the display.

The transmit power level used is set to provide the desired pressure level for a given situation. The signal amplitude, aperture, f number, apodization, or other characteristics of the transmit event are configured to provide the transmit power level.

FIG. 4 shows an ultrasound system for adaptive acoustic pressure estimation in medical ultrasound. The system implements the method of FIG. 1 or another method. The system includes a transducer 12, a transmit amplifier 14, a receive beamformer 16, an image processor 18, a processor 22, a display 20, and a memory 22. Additional, different or fewer components may be provided, such a multiple detectors associated with B-mode and flow imaging. In one embodiment, the system is a medical diagnostic ultrasound system. In another embodiment, the system is a therapeutic ultrasound system. In other embodiments, the system is a computer or server.

The transducer 12 is a single element or multiple elements of piezoelectric material. In alternative embodiments, the transducer 12 comprises capacitive membrane structures. For multiple elements, the transducer 12 is a linear, curved linear or multidimensional array. Other transducers for converting between electrical and acoustic energy can be used. The transducer 12 generates acoustic energy in response to electrical waveforms. The acoustic waveforms are output at powers set by the transmit amplifier 14. The transducer 12 generates receive signals in response to acoustic echoes, such as for measuring response to transmitted acoustic energy.

The transmit amplifier 14 connects with the transducer 12 and is a variable amplifier, digital-to-analog converter or other analog or digital device for changing or increasing a power, peak voltage or other power characteristic of a transmit waveform. In alternative embodiments, the transmit amplifier 14 comprises a voltage divider or other device for reducing the power associated with the transmit waveform. A separate transmit amplifier 14 is provided for each system channel or transducer element, but one transmit amplifier 14 may be used for a plurality of channels or elements. In one embodiment, the transmit amplifier 14 applies apodization for transmitting along a beam and is included as part of a transmit beamformer.

The transmit waveforms output from the transmit amplifier 14 are converted to acoustic energy by the transducer 12. Echo signals responsive to the acoustic energy and any contrast agents are received by the transducer 12. The transducer 12 converts the echo signals into electrical signals or data.

The echo signals are beamformed by the receive beamformer 16. Relative delays or phase and apodization are applied to the signals for the receive aperture. Over time or for different depths, the relative delays and/or phasing varies, providing dynamic receive focusing. The signals are combined, such as summed, to beamform. The resulting samples or data represent locations at different depths along a line. Data includes one or more digital samples or analog information.

For isolating or distinguishing information at different frequencies, the receive beamformer 16 includes a filter. Using a memory, the same data may be filtered multiple times. Parallel filtering is provided in other embodiments. The filter may be a programmable filter or fixed filter. For example, high pass and low pass filters are provided for separating fundamental and harmonic information. As another example, one or more band pass filters or series low pass and high pass filters are used. Alternatively, the filter includes memories or buffers with or without multipliers for summing or differencing receive data associated with different phase, amplitude, and/or polarity on transmit. Pulse inversion, amplitude coding, or other frequency isolating combination is performed. Other techniques and corresponding filters for identifying information at a harmonic, including sub-harmonics (e.g. ½f), fractional harmonics (3/2f) and/or integer harmonics (e.g. 2f), of a fundamental transmit frequency band (f) may be used.

After receive beamformation or other receiving technique, data is provided to the image processor 18 or to the processor 22. Where the responses for estimating acoustic pressure use intensity values, the data is detected prior to estimating. Alternatively, the processor 22 estimates the pressure based on the beamformed data prior to detection.

The image processor 18 is a contrast agent detector, B-mode detector, Doppler detector, flow detector or other detector for detecting one or more characteristics of returned signals. The image processor 18 may be a same detector used for imaging contrast agents. Alternatively, the image processor 18 is combined with the processor 22 and used for setting the transmit power and is separate from detectors for imaging.

The processor 22 is one or more of an application specific integrated circuit, a general processor, a digital signal processor, a control processor, analog circuit, digital circuit, field programmable gate array, graphics processing unit, combinations thereof, or other device operable to set a transmit power of the transmit amplifier 14. The processor 22 controls operation of the transmit beamformer 14, the receive beamformer 16, and/or the image processor 18 to obtain responses at different frequencies and other information used to estimate the pressure and/or set the transmit level. The processor 22 is configured by software, hardware, design, or combinations thereof.

The processor 22 is configured to establish a transmit power of the transmit amplifier 14 as a function of amplitude profiles as a function of depth at two or more frequencies. Profiles associated with different transmit foci and/or different transmit power levels may be used as well in other embodiments. Using a stored attenuation, measured attenuation, stored non-linearity parameter value, and/or a measured non-linearity parameter value, the processor 22 estimates, with the amplitude profiles, an acoustic pressure through application of a model. The acoustic pressure is estimated for one or more locations. Pressure at other locations may be estimated, extrapolated, interpolated, and/or calculated.

Using an optimization process or function, the transmit power level for use in further transmissions is set based on the acoustic pressure. The processor 22 is configured to set the transmit power level. Other information may be used for setting the level, such as noise and application information.

The memory 24 stores look-up tables, databases, or other model information. Output pressures, transmit levels, transmit characteristics (e.g., aperture, apodization, focal zone, delay profile, and/or f number), or other outputs are stored. The output values are looked-up based on input values stored in the memory 24. The transmit power levels and/or pressure estimates are selectable based on the input amplitude profiles with or without other information. Alternatively, the memory 24 stores an algorithm or other function for calculating the pressure or transmit level based on inputs.

The instructions for implementing the processes, methods and/or techniques discussed above are provided on non-transitory computer-readable storage media or memories 24, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 20 is a monitor, liquid crystal display, plasma screen, projector, touch screen, flat screen, printer, or other device for outputting information to the user. The display 20 may generate an image, such as an image of contrast agent response to ultrasound. The image may include an estimated pressure or set transmit level.

While the invention has been described above by reference to various embodiments, it should be understood that many changes and modifications can be made without departing from the scope of the invention. It is therefore intended that the foregoing detailed description be understood as an illustration of the presently preferred embodiment of the invention, and not as a definition of the invention. It is only the following claims, including all equivalents, which are intended to define the scope of this invention.

What is claimed is:

1. A method for adaptive acoustic pressure estimation in medical ultrasound, the method comprising:
    acquiring first responses of tissue at a first frequency for a plurality of locations;
    acquiring second responses of the tissue at a second frequency for the plurality of locations;
    estimating, by a processor, an acoustic pressure at at least one of the locations, the acoustic pressure estimated as a function of the first and second responses; and
    setting an acoustic output of a transducer as a function of the acoustic pressure.

2. The method of claim 1 wherein acquiring the first and second responses comprises acquiring at a fundamental and a second harmonic frequency, respectively.

3. The method of claim 1 wherein acquiring the first and second responses comprises acquiring along a line, the locations comprising sample positions along the line.

4. The method of claim 1 wherein acquiring the first and second responses each comprise acquiring amplitude as a function of depth with a same transmit focal location.

5. The method of claim 1 wherein acquiring the first responses comprise acquiring in response to different transmit powers, and wherein acquiring the second responses comprises acquiring in response to the different transmit powers.

6. The method of claim 1 wherein estimating comprises estimating as a function of attenuation.

7. The method of claim 6 further comprising:
determining attenuation from a slope of the first responses.

8. The method of claim 1 wherein estimating comprises estimating as a function of an ultrasound non-linear parameter of tissue for the locations.

9. The method of claim 1 wherein estimating comprises inputting the first and second responses into a model and outputting the acoustic pressure from the model.

10. The method of claim 1 wherein estimating comprises looking up the acoustic pressure based on a combination of two or more of the first responses, second responses, a first parameter value derived from the first responses, or a second parameter value derived from the second responses.

11. The method of claim 1 wherein estimating comprises estimating the acoustic pressure at a first location of the plurality;
further comprising:
determining acoustic pressure at other locations than the first location of the plurality, the determining being a function of the acoustic pressure at the first location.

12. The method of claim 1 wherein setting comprises setting the acoustic output to avoid destruction of contrast agents while having a substantially maximum output.

13. The method of claim 1 wherein setting comprises setting the acoustic output as a function of the acoustic pressure and a thermal dose.

14. The method of claim 1 wherein setting comprises:
measuring noise; and
setting a transmit power as a function of the acoustic pressure and the noise.

15. In a non-transitory computer readable storage medium having stored therein data representing instructions executable by a programmed processor for adaptive acoustic pressure estimation in medical ultrasound, the storage medium comprising instructions for:
determining tissue response in first and second frequency bands to acoustic energy;
setting a transmit power as a function of an acoustic pressure, the acoustic pressure estimated as a function of the tissue response in the first and second frequency bands; and
performing contrast agent imaging or acoustic therapy using the transmit power.

16. The non-transitory computer readable storage medium of claim 15 wherein determining the tissue response comprises determining the tissue response at different depths in response to different transmit levels for each of the first and second frequency bands.

17. The non-transitory computer readable storage medium of claim 15 wherein setting comprises:
estimating the acoustic pressure as a function of the tissue response, an attenuation, and an ultrasound non-linearity parameter; and
setting the transmit power as a function of the acoustic pressure.

18. An ultrasound system for adaptive acoustic pressure estimation in medical ultrasound, the system comprising:
a transducer;
a transmit amplifier connected with the transducer; and
a processor configured to establish a transmit power of the transmit amplifier as a function of an acoustic pressure, the acoustic pressure estimated as a function of a first amplitude profile as a function of depth at a first frequency and a second amplitude profile as a function of depth at a second frequency different than the first frequency.

19. The system of claim 18 further comprising a memory, the memory storing transmit powers including the established transmit power selectable as a function of the first and second amplitude profiles or as a function of parameter values derived from the first and second amplitude profiles.

* * * * *